United States Patent [19]

Uhrhan et al.

[11] 4,393,206

[45] Jul. 12, 1983

[54] PROCESS FOR THE PRODUCTION OF 2,3-DIHYDRO-4H-1,4-BENZOTHIAZINES

[75] Inventors: Paul Uhrhan, Odenthal; Edmund Krauthausen, Cologne, both of Fed. Rep. of Germany

[73] Assignee: Bayer Aktiengesellschaft, Leverkusen, Fed. Rep. of Germany

[21] Appl. No.: 359,221

[22] Filed: Mar. 18, 1982

[30] Foreign Application Priority Data

Mar. 24, 1981 [DE] Fed. Rep. of Germany ....... 3111487

[51] Int. Cl.$^3$ .......................................... C07D 279/16
[52] U.S. Cl. .................................................. 544/51
[58] Field of Search ........................................ 544/51

[56] References Cited

PUBLICATIONS

Monatshefte Für Chemie, vol. 88, Edition 5, pp. 822–829, (1957).

*Primary Examiner*—John M. Ford
*Attorney, Agent, or Firm*—Connolly and Hutz

[57] ABSTRACT

Process for the preparation of 2,3-Dihydro-4H-1,4-benzothiazines by cyclisation of suitable 2-(2-Hydroxyalkyl)-thioanilines under elimination of water in the presence of phosphorous acid.

6 Claims, No Drawings

PROCESS FOR THE PRODUCTION OF 2,3-DIHYDRO-4H-1,4-BENZOTHIAZINES

This invention relates to a process for the production of 2,3-dihydro-4H-1,4-benzothiazines.

It is known to produce 2,3-dihydro-4H-1,4-benzothiazine by reacting 2-aminothiophenol with 1,2-dibromoethane in the presence of potassium hydroxide. However, the yield is small (N. A. Langlet, Bihang. till Svenska Vet. -Akad. Handlinger 22 II, No. 1, P. 8; see also Beilstein XXII, 4th edition, p. 34 (1937)). Ethylene-bis-2-aminophenyl sulphide is produced as the main product (see O. Hromatka, M Vaculny, J. Augl and K. Wiltschke, Mh. Chem. 88, 822, 1957; E. Fromm, H. Benzinger and F. Schafer, Ann. Chem. 394 332, 1912).

It is also known to produce 2,3-dihydro-4H-1,4-benzothiazines by reducing corresponding 3-oxo-dihydro-1,4-benzothiazines using lithium aluminum hydride (see, for example, O. Hromatka and Mitarbeiter, Mh. Chem. 88, 822, 1957; J. F. Kerwin, J. E. McCarty and C. A. Vander, J. Org. Chem. 24, 1719, 1959), but lithium aluminium hydride cannot be handled safely and necessitates the exclusion of moisture. Moreover, only 3-unsubstituted benzothiazine derivatives are accessible using this method.

According to Culvenor and colleagues, dihydrobenzothiazines should be easily accessible by the reaction of 2-aminothiophenol with oxiranes in alcoholic potash lye (C. C. L. Culvenor, W. Davies and N. S. Heath, J. Chem. Soc. (London) 1949, 278). 2,3-dihydro-4H-1,4-benzothiazine should also be produced during the reduction of 2-hydroxyethyl-2-nitrophenyl sulphide using tin and hydrochloric acid (R. Fusco and G. Palazzo, Gazz. chim. ital. 81, 735, 1951). However, in both cases it was subsequently proved that the authors only had the corresponding 2-hydroxyalkyl-thioanilines (O. Hromatka, M. Vaculny, H. Augl and K. Wiltschke, Mh. Chem. 88, 822, 1957; O. Hromatka. J. Augl, A. Brazda and W. Grunsteidl. Mh. Chem. 90, 544, 1959).

In French Patent No. 1,344,437, 2,3-dihydro-4H-1,4-benzothiazines are described as ozone-protection agents for elastomers. Culvenor's method was quoted as a possible production, but it does not produce benzothiazines and the reaction of 2-amino-thiophenols with 1,2-dihalogen alkanes or chlorhydrins was also mentioned, but without details of yields or synthesis examples being specified.

It has now been found that it is possible to produce 2,3-dihydro-4H-1,4-benzothiazines by cyclising 2-(2-hydroxyalkyl)-thioanilines using phosphorous acid with the release of water.

Suitable concentrations of phosphorous acid range from 0.1 to 100, preferably from 5 to 25%, by weight, based on the 2-(2-hydroxyalkyl)-thioaniline used.

Compounds corresponding to the following general formula (I) may be used as 2-(2-hydroxyalkyl)-thioanilines for the process according to the present invention:

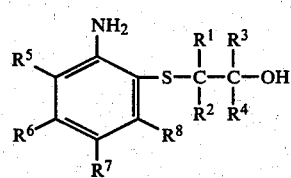

(I)

wherein
$R^1$ to $R^4$, which may be the same or different, each represents hydrogen, lower alkyl having from 1 to 4 carbon atoms, optionally substituted cycloalkyl having from 5 to 8 carbon atoms, aralkyl having from 7 to 11 carbon atoms or aryl, or
$R^1$ and $R^2$ or $R^3$ and $R^4$ together with the carbon atom to which they are attached may complete a cycloalkyl radical having from 5 to 8 carbon atoms, or one of the radicals $R^3$ and $R^4$ together with $R^1$ or $R^2$ may represent an alkylene radical having from 3 to 6 carbon atoms. $R^6$ and $R^8$, which may be the same or different, each represents hydrogen, halogen, nitro, linear or branched alkyl having from 1 to 12 carbon atoms, linear or branched alkenyl having from 2 to 12 carbon atoms, aralkyl having from 7 to 11 carbon atoms, cycloalkyl having from 5 to 8 carbon atoms, and
$R^5$ and $R^7$, which may be the same or different, each represents hydrogen, halogen, nitro, linear or branched alkyl having from 1 to 12 carbon atoms, linear or branched alkenyl having from 2 to 12 carbon atoms, cycloalkyl having from 5 to 8 carbon atoms, aralkyl having from 7 to 11 carbon atoms, alkoxy, the radical:

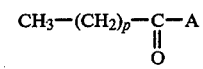

wherein
P represents an integer of from 0 to 20, preferably from 8 to 16, and
A represents $-(CH_2)_q-$, $-O-(CH_2)_q-$, $-NH-(CH_2)_q-$ or $-S-(CH_2)_q-$ wherein
q represents 0 to 4, preferably 0 or 1, or the radical:

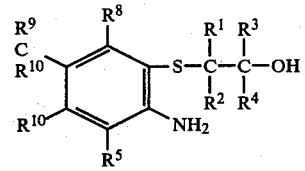

wherein
$R^1$ and $R^6$ and $R^8$ represent the above-mentioned radicals, and
$R^9$ and $R^{10}$ independently represent hydrogen, optionally substituted aryl, linear or branched alkyl having from 1 to 12 carbon atoms, cycloalkyl or cycloalkenyl having from 5 to 8 carbon atoms, or
$R^9$ and $R^{10}$ together with the carbon atom to which they are attached complete a cycloalkyl radical having from 5 to 7 carbon atoms.

The resulting 2,3-dihydrobenzothiazines correspond to the following general formula (II):

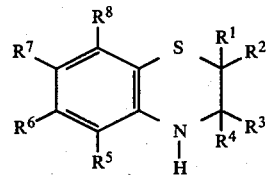

(II)

wherein $R^1$ to $R^8$ are as defined above.

Compounds corresponding to general formula (I) are preferred for the process according to the present invention, in which formula, R$^1$ and R$^2$ represent hydrogen or lower alkyl having from 1 to 4 carbon atoms, and R$^3$ and R$^4$ represent lower alkyl, and R$^5$ to R$^8$ are as defined above.

R$^1$, R$^2$ and R$^5$ to R$^8$ most preferably independently represent hydrogen or methyl, and R$^3$ and R$^4$ most preferably represent methyl.

The following are mentioned as particular examples of the 2-(2-hydroxyalkyl)-thioanilines: 2-(2-hydroxyalkyl)-thioaniline, 2-(2-hydroxy-propyl-)thioaniline, 2-(2-hydroxy-1-methylethyl-)thioaniline, 2-(1,2-dimethyl-2-hydroxypropyl)-thioaniline, 2-(2-hydroxy-1-methylpropyl)-thioaniline, 2-(2-hydroxy-2-methylpropyl)-thioaniline, 2-(2-hydroxy-1,1,2-trimethylpropyl)-thioaniline, 2-(2-hydroxybutyl)-thioaniline, 2-(2-hydroxypentyl)-thioaniline, 2-(2-hydroxycyclohexyl)thioaniline, 2-(2-hydroxycyclooctyl)-thioaniline, 2-(1,2-diphenyl-2-hydroxyethyl)-thioaniline, 2-(2-hydroxy-1-phenylethyl)-thioaniline, 2-(2-hydroxy-2-phenylethyl)thioaniline, 2-(2-hydroxy-2-phenylpropyl-)-thioaniline, 2-(2,2-diphenyl-2-hydroxyethyl)-thioaniline, 3,5-dichloro-2-(2-hydroxyethyl)-thioaniline, 3,5-dichloro-2-(2-hydroxypropyl)-thioaniline, 3,5-dichloro-2-(2-hydroxy-2-methylpropyl)-thioaniline, 3,5-dichloro-2-(2-hydroxy-2-phenylpropyl)-thioaniline, 4-chloro-2-(2-hydroxy-2-methylpropyl)-thioaniline, 5-chloro-2-hydroxy-2-methylcyclohexyl)-thioaniline, 4-carboethoxy-2-(2-hydroxy-1,1,2-trimethylpropyl)-thioaniline, 2-(2-hydroxyethyl)-thio-4-methoxy-aniline, 4,4'-diamino-3,3'-di-(2-hydroxy-1,2-dimethylpropyl)-thio-diphenylmethane, 4,4'-diamino-3,3'-di-(2-hydroxyethyl)-thio-diphenylmethane, 2,2-di[4-amino-3-(2-hydroxy-2-methylpropyl)-thio-phenyl]propane, 4,6-di-(1-phenylethyl)-2-(2-hydroxy-2-methylpropyl)-thioaniline, 2-(2-hydroxyethyl)-thio-4-nitroaniline, 2-(2-hydroxy-2-methylpropyl)-thio-5-nitroaniline, 2-(2-hydroxyethylthio)-4-stearoyl-aniline, 2-(2-hydroxy-2-methylpropylthio)-4-hexadecanoyl-aniline, octadecanoic acid-4-amino-3-(2-hydroxy-2-phenylpropylthio)-benzylester, 3-ethoxy-5-bromo-6-methyl-2-(2-hydroxy-1-methyl-2-cyclopentyl-3-ethyl-pentylthio)-aniline,

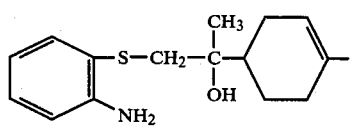

2-[2-hydroxy-2-(4-methylcyclohex-3-enyl)-propylthio]-aniline,

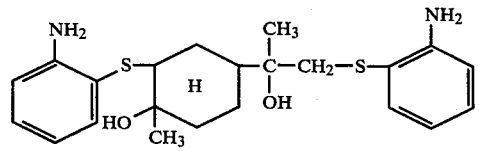

2-[2-hydroxy-2-(3-o-aminophenylthio-4-hydroxy-4-methylcyclohexyl)-propylthio]-aniline.

The formation of 2,3-dihydro-4H-1,4-benzothiazines from 2-(2-hydroxyalkylthio)-anilines may be explained with reference to the following equation:

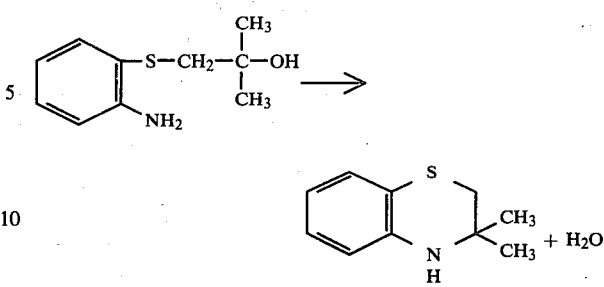

The reaction may be carried out at a temperature of from 60° to 300° C., preferably from 100° to 200° C., and the process may be carried out under normal pressure, elevated or reduced pressure, preferably under normal pressure. It has proved to be advantageous to remove the water produced during the reaction from the mixture. This may be effected, for example, by distilling this water out of the mixture at an elevated temperature and/or under reduced pressure. A suitable organic solvent is preferably used as an entrainer for this purpose. Those solvents are suitable which boil azeotropically together with water. Water-immiscible solvents are particularly preferred, for example, toluene, xylene, chloroform and carbon tetrachloride. In a particular embodiment, the distillate of the entrainer and water may be separated and the entrainer may be returned into the distillation or reaction.

The 2,3-dihydro-4H-1,4-benzothiazines produced according to the present process may be used as ozone-protection agents for elastomers (see French Patent No. 1,344,437), as intermediate products for the production of highly-active stabilizers for organic compounds, as intermediate products or dyes (see McNally and Dickey, U.S. Pat. No. 2,251,945), as intermediate products for the preparation of antimycotics (see Boshagen and Plempel, U.S. Pat. No. 3,991,126) or as very efficient ageing protection agents for polymers, with the advantage that they do not discolour, or only very slightly discolour the polymers stabilized therewith.

The following Examples illustrate the process according to the present invention.

EXAMPLES

Example 1

18.25 kg of 2-(2-hydroxy-2-methylpropylthio)-aniline (obtained according to the method of Colvenor et al, J. Chem. Soc. 1949, 278 ff, from 2-amino-thiophenol, potassium hydroxide and isobutene oxide having a boiling point of from 131°–9° C./0.1 mbar, melting point of from 45° to 49° C.) are heated for 2 hours with 1.85 kg of xylene and 2.08 kg of 73% phosphorous acid in a water separator. The mixture is then neutralised using 2.775 kg (69.4 mols) of sodium hydroxide in 12 kg of water, the organic phase is separated and the solvent is removed under vacuum. After distillation, 10.76 kg of 3,3-dimethyl-2,3-dihydro-4H-1,4-benzothiazine are obtained having a boiling point of from 110° to 115° C./0.4 mbar, melting point of from 52° to 55° C. The mass spectrum shows a molecular ion at 179 (64% relative intensity) and as main fragments 164 (100%) and 149 (30%).

Example 2

Analogously to Example 1, the required 2,2,3,3-tetramethyl-2,3-dihydro-4H-1,4-benzothiazine is obtained as a colourless oil having a boiling point of 89° C./0.04 mbar using 2-(2-hydroxy-1,1,2-trimethylpropylthio)-aniline, melting point of from 60° to 62° C., boiling point of 125° C./0.1 mbar (obtained from tetramethyloxirane and 2-aminothiophenol). $n_D^{20} = 1.5955$; the mass spectrum shows a molecular ion at 207 (74% relative intensity) and as main fragments 192 (24%), 177 (14%), 164 (100%), 150 (44%), 132 (70%), 125 (24%), 109 (15%), 92 (22%), 42 (17%) and 41 (16%).

Example 3

90 g (0.5 mols) of limonene diepoxide are added drop-wise to a solution of 125 g (1 mol) of 2-aminothiophenol, 41 g (1.025 mols) of sodium hydroxide and 200 ml of water at 50° C. A cloudy resinous deposit is formed which is separated, washed and freed from adhering volatile constituents under vacuum at 70° C. 140 g of a light-yellow viscous oil is obtained which is mixed with 100 ml of xylene and 14 g of 73% phosphorous acid and is boiled for 6 hours in a water separator. After neutralising using soda lye, the organic phase is separated and the solution is removed under vacuum. 75 g of a brown, brittle powder is obtained which contains as the main constituent 10a-methyl-3-(3-methyl-2,3-dihydro-4H-1,4-benzothiazine-3-yl)-1,2,3,4,4a,10a-hexahydrophenothiazine. The mass spectrum shows as a molecular ion 387 (12% relative intensity) and as main fragments 258 (40%), 218 (30%), 164 (100%), 149 (19%), 136 (17%), 133 (20%), 125 (28%) and 124 (27%).

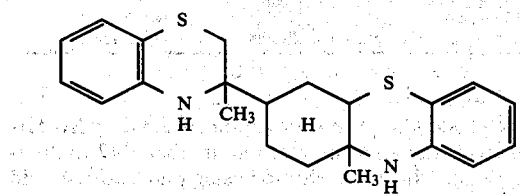

Example 4

34 g (0.2 mols) of 4- or 5-nitro-2-thioaniline (mixture) and 8.2 g (0.205 mols) of sodium hydroxide in 150 ml of water are mixed with 14.4 g (0.2 mols) of isobutene oxide with cooling, are subsequently stirred for 3 hours and then filtered under suction. 46 g of 2-(2-hydroxy-2,2-dimethylethyl)-thio-4- or 5-nitroaniline are obtained as an olive-brown powder having a melting point of from 77° to 90° C., the mass spectrum of which shows a molecular ion at 242 (31% relative intensity) and as main fragments 184 (59%), 167 (100%), 137 (39%) and 59 (75%). After cyclisation using phosphorous acid in xylene, as described in Example 1, an undistillable dark-brown viscous oil is obtained which, according to the spectra, mainly consists of 3,3-dimethyl-6- or 7-nitro-2,3-dihydro-4H-1,4-benzothiazine. The mass spectrum shows a molecular ion at 224 (100% relative intensity) and the following as main fragments: 209 (87%), 181 (92%), 169 (41%), 163 (34%) and 55 (76%).

Examples 5 to 7 shows the commercial utility of the compounds produced by the process according to the present invention as intermediate products for the preparation of stabilizers.

Example 5

112 g (1 mol) of diisobutylene are added drop-wise to 90 g (0.5 mol) of the product from Example 1 and 10 g of aluminium trichloride at 100° C. and are then stirred for 6 hours at this temperature. The reaction mixture is poured into ice water, the deposit is filtered under suction and is introduced into soda lye. The organic layer is separated, freed from unreacted material under high vacuum and the residue is recrystallised from methanol/water. 3,3-dimethyl-7-(1,1,3,3-tetramethyl-butyl)-2,3-dihydro-4H-1,4-benzothiazine is obtained having a melting point of from 60° to 62° C. The mass spectrum shows a molecular ion at 219 (13% relative intensity) and a main fragment at 220 (100%).

Example 6

Analogously to Example 5, 92 g of 3,3-dimethyl-5,7-di-(1-methyl-1-phenylethyl)-2,3-dihydro-4H-1,4-benzothiazine are obtained as a yellow oil using α-methyl styrene instead of diisobutylene. The mass spectrum shows a molecular ion at 415 (91% relative intensity) and the following as main fragments: 400 (100%), 322 (11%), 119 (38%), 103 (11%) and 91 (31%).

Example 7

12 g of 2,2,3,3-tetramethyl-2,3-dihydro-4H-1,4-benzothiazine (Example 2), 25 ml of methanol and 2 drops of concentrated sulphuric acid are introduced and 2.4 g of 37% aqueous formaldehyde solution are added drop-wise at 30° C. The mixture is refluxed for 2 hours, neutralised using aqueous soda lye and refluxed for a further 3 hours. The solvent is then substantially distilled off under vacuum, the residue is taken up in methylene chloride and washed twice with water. The solvent is distilled off and 8.2 g of di-(2,2,3,3-tetramethyl-2,3-dihydro-4H-1,4-benzothiazine-7-yl)-methane is obtained as a tough resin. The mass spectrum shows a molecular ion at 426 (94% relative intensity) and the main fragments 411 (18%) and 383 (100%). In addition thereto, the product still contains small quantities of compounds containing three and four (2,2,3,3-tetramethyl-2,3-dihydro-4H-1,4-benzothiazine) nuclei having the molecular masses of 645 and 864.

Example 8

Example 8 shows the commercial utility as stabilisers in rubber.

The following natural rubber mixture was prepared on a roller:

|  | Parts, by weight |
|---|---|
| Light crêpe | 100.00 |
| Zinc oxide | 10.0 |
| Stearic acid | 1.0 |
| Titanium dioxide | 10.0 |
| Blank fix | 60.5 |
| Tetramethyl thiuram disulphide | 0.5 |
| Sulphur | 2.0 |
| Stabilizer | as specified in Table 1. |

The mixture was vulcanised in a press for 15 minutes at 130° C. The resulting vulcanisate was aged in an oxygen tank (according to Bierer-Davis) at 21 bars oxygen and at 70° C. (DIN 53 508). The results are given in Table 1 and they indicate the suitability of the compounds produced by the process according to the present invention as stabilizers or as intermediates for stabilizers.

TABLE 1

(a) without ageing protection agent (comparison)

| | Strength (mPa) | Expansion (%) | Modulus at 450% expansion (mPa) | Elasticity 20° C./70° C. (%) | | Hardness 20° C./70° C. (Shore A) | |
|---|---|---|---|---|---|---|---|
| Before ageing: | 22.7 | 730 | 8.1 | 74 | 79 | 52 | 53 |
| After ageing for 7 days: | 5.0 | 470 | — | — | 50 | 47 | 35 |
| After ageing for 14 days: | destroyed. | | | | | | |
| Colour of the vulcanisates: | | | | | | | |
| Before exposure | white | | | | | | |
| After exposing to daylight for 2 months | white | | | | | | |

(b) Polymerised with 1 part, by weight, of 2,2,4-trimethyl-1,2-dihydroquinoline (comparison)

| | Strength | Expansion | Modulus | Elasticity | | Hardness | |
|---|---|---|---|---|---|---|---|
| Before ageing: | 23.8 | 710 | 9.6 | 75 | 81 | 54 | 53 |
| After ageing for: 7 days: | 16.8 | 580 | 11.5 | 72 | 79 | 56 | 55 |
| After ageing for 14 days: | 14.4 | 570 | 10.4 | 66 | 75 | 54 | 53 |
| After ageing for 21 days: | 11.9 | 540 | 9.8 | 55 | 63 | 53 | 50 |
| Colour of the vulcanisates: | | | | | | | |
| Before exposure | pink | | | | | | |
| After exposing to daylight for 2 months | light brown | | | | | | |

(c) With 1 part, by weight, of alkyl- and aralkyl-substituted phenols (comparison)

| | Strength | Expansion | Modulus | Elasticity | | Hardness | |
|---|---|---|---|---|---|---|---|
| Before ageing: | 23.0 | 730 | 8.0 | 74 | 81 | 52 | 52 |
| After ageing for 7 days: | 14.6 | 600 | 8.9 | 65 | 69 | 52 | 50 |
| After ageing for 14 days: | 9.3 | 560 | 7.1 | 57 | 56 | 46 | 38 |
| After ageing for 21 days: | destroyed | | | | | | |
| Colour of the vulcanisates: | | | | | | | |
| Before exposure | white | | | | | | |
| After exposing to daylight for 2 months | white | | | | | | |

(d) With 1 part, by weight, of 2,2'-methylene-bis-(4-methyl-6-t-butyl-phenol) (comparison)

| | Strength | Expansion | Modulus | Elasticity | | Hardness | |
|---|---|---|---|---|---|---|---|
| Before ageing: | 22.8 | 750 | 7.5 | 74 | 79 | 51 | 51 |
| After ageing for 7 days: | 17.8 | 650 | 9.6 | 63 | 77 | 52 | 51 |
| After ageing for 14 days: | 15.4 | 600 | 9.7 | 62 | 67 | 49 | 48 |
| After ageing for 21 days: | 13.2 | 610 | 8.8 | 57 | 65 | 47 | 45 |
| Colour of the vulcanisates: | | | | | | | |
| Before exposure | white | | | | | | |
| After exposing to daylight for 2 months | pink | | | | | | |

(e) With 1 part, by weight of stabiliser from Example 1

| | Strength | Expansion | Modulus | Elasticity | | Hardness | |
|---|---|---|---|---|---|---|---|
| Before ageing | 21.4 | 750 | 5.7 | 73 | 79 | 49 | 48 |
| After ageing for 14 days: | 12.2 | 630 | 6.6 | 57 | 66 | 46 | 47 |
| After ageing for 21 days: | 8.8 | 600 | 5.4 | 53 | 63 | 45 | 45 |
| Colour of the vulcanisates: | | | | | | | |
| Before exposure | white | | | | | | |
| After exposing to daylight for 2 months | cream | | | | | | |

(f) With 1 part, by weight, of stabilizer from Example 5

| | Strength | Expansion | Modulus | Elasticity | | Hardness | |
|---|---|---|---|---|---|---|---|
| Before ageing | 23.6 | 740 | 8.4 | 74 | 81 | 52 | 52 |
| After ageing for 7 days: | 19.4 | 620 | 11.2 | 70 | 76 | 55 | 55 |
| After ageing for 14 days: | 14.2 | 550 | 10.9 | 64 | 73 | 53 | 52 |
| After ageing for 21 days: | 11.5 | 530 | 9.8 | 58 | 69 | 51 | 48 |
| Colour of the vulcanisates: | | | | | | | |
| Before exposure | white | | | | | | |
| After exposing to daylight for 2 months | light cream | | | | | | |

(g) With 1 part, by weight, of stabiliser from Example 6

| | Strength | Expansion | Modulus | Elasticity | Hardness |
|---|---|---|---|---|---|
| Before ageing | 22.9 | 730 | 8.7 | 73  79 | 49  50 |
| After ageing for 7 days: | 14.1 | 620 | 8.9 | 60  70 | 51  51 |
| After ageing for 14 days: | 9.4 | 580 | 6.9 | 49  56 | 46  39 |
| After ageing for 21 days: | destroyed | | | | |
| Colour of the vulcanisates: | | | | | |
| Before exposure | white | | | | |
| After exposing to daylight for 2 months | light cream | | | | |

We claim:

1. A process for the production of 2,3-dihydro-4H-1,4-benzothiazines, characterised in that 2-(2-hydroxyalkyl)-thioanilines are cyclised using phosphorous acid with the release of water.

2. A process according to claim 1, characterised in that 2-(2-hydroxyalkyl)-thioanilines corresponding to the following general formula (I) are cyclised:

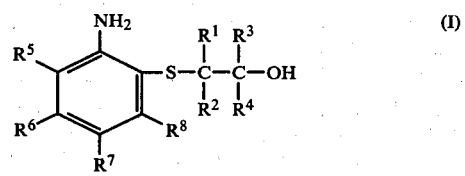

wherein
$R^1$ to $R^4$, which may be the same or different, each represents hydrogen, lower alkyl having from 1 to 4 carbon atoms, cycloalkyl having from 5 to 8 carbon atoms, aralkyl having from 7 to 11 carbon atoms or aryl, or
$R^1$ and $R^2$ or $R^3$ and $R^4$ together with the carbon atom to which they are attached complete a cycloalkyl radical having from 5 to 8 carbon atoms, or one of $R^3$ and $R^4$ together with $R^1$ or $R^2$ may represent an alkylene radical having from 3 to 6 carbon atoms,
$R^6$ and $R^8$, which may be the same or different, each represents hydrogen, halogen, nitro, linear or branched alkyl having from 1 to 12 carbon atoms, linear or branched alkenyl having from 2 to 12 carbon atoms, aralkyl having from 7 to 11 carbon atoms, cycloalkyl having from 5 to 8 carbon atoms or alkoxy, and $R^5$ and $R^7$, which may be the same or different, each represents hydrogen, halogen, nitro, linear or branched alkyl having from 1 to 12 carbon atoms, linear or branched alkenyl having from 2 to 12 carbon atoms, cycloalkyl having from 5 to 8 carbon atoms, aralkyl having from 7 to 11 carbon atoms, alkoxy, the radical:

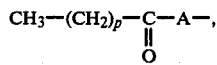

wherein
p represents an integer of from 0 to 20, preferably from 8 to 16, and
A represents —$(CH_2)_q$—, —O—$(CH_2)_q$—, —NH—$(CH_2)_q$— or —S—$(CH_2)_q$— wherein
q represents 0 to 4, preferably 0 or 1, or the radical:

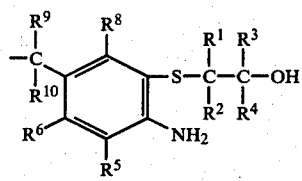

wherein $R^1$ to $R^6$ and $R^8$ are as defined above, and
$R^9$ and $R^{10}$ independently represent hydrogen, optionally substituted aryl, linear or branched alkyl having from 1 to 12 carbon atoms, cycloalkyl or cycloalkenyl having from 5 to 8 carbon atoms, or
$R^9$ and $R^{10}$ together with the carbon atom to which they are attached complete a cycloalkyl radical having from 5 to 7 carbon atoms, using phosphorous acid with the release of water, into 2,3-dihydro-4H-1,4-benzothiazines corresponding to the following general formula (II):

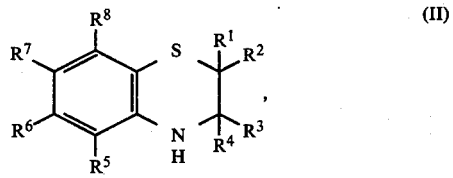

wherein $R^1$ to $R^8$ are as defined above.

3. A process according to claim 1, characterised in that water is split off at from 100° to 200° C.

4. A process according to claim 1, characterised in that the water produced by the reaction is removed from the reaction mixture.

5. A process according to claim 1, characterised in that the water is split off in the presence of from 0.1 to 100%, by weight, of phosphorous acid.

6. A process according to claim 1, characterised in that the water is split off in the presence of from 5 to 25%, by weight, of phosphorous acid.

* * * * *